United States Patent [19]

Mlot-Fijalkowski

[11] 4,281,033
[45] Jul. 28, 1981

[54] FLUORESCENT PENETRANT SYSTEM

[75] Inventor: Adolf Mlot-Fijalkowski, Lincolnwood, Ill.

[73] Assignee: Magnaflux Corporation, Chicago, Ill.

[21] Appl. No.: 129,726

[22] Filed: Mar. 12, 1980

[51] Int. Cl.³ ........................ B05D 7/24; C09K 11/00
[52] U.S. Cl. ..................................... 427/157; 427/8; 427/9
[58] Field of Search ............................. 427/8, 9, 157

[56] References Cited

U.S. PATENT DOCUMENTS

| | | | |
|---|---|---|---|
| 3,558,882 | 1/1971 | Mlot-Fijalkowski | 250/71 |
| 3,845,658 | 11/1974 | Conway et al. | 427/8 X |
| 3,930,063 | 12/1975 | Miller et al. | 427/8 X |
| 4,116,634 | 9/1978 | Nieberlein | 427/8 X |

*Primary Examiner*—James R. Hoffman
*Attorney, Agent, or Firm*—Hill, Van Santen, Steadman, Chiara & Simpson

[57] ABSTRACT

A method for non-destructive testing for flaws on the surface of a workpiece which includes the step of applying a penetrant composition including a fluorescent dye in a liquid vehicle onto the surface to permit the penetrant to become trapped in the flaws and then removing excess penetrant from the surface while leaving penetrant entrapped in such flaws. A remover is then applied to the surface, the remover composition including a solvent, at least one surface active agent which serves as an emulsifier for the liquid vehicle of entrapped penetrant, and a fluorescent material which is more readily soluble in the liquid vehicle of the penetrant than it is in the solvent. Upon contact of the entrapped penetrant with the remover, the fluorescent material from the remover is preferentially absorbed in the penetrant vehicle entrapped in the flaws thereby enhancing the fluorescent indication provided by the entrapped penetrant. The indications are developed in the usual way by applying a developer to the surface to draw the entrapped penetrant to the surface of the workpiece where it is contrastingly visible to the surface and is observable by viewing the surface under ultraviolet light.

7 Claims, No Drawings

FLUORESCENT PENETRANT SYSTEM

BACKGROUND OF THE INVENTION

1. Field of the Invention

The present invention is in the field of non-destructive testing processes employing the penetrant inspection process. The improvement resides in incorporating a fluorescent material in the remover to supplement or reinforce the fluorescent capability of the fluorescent dye contained in the penetrant which has become lodged in surface flaws.

2. Description of the Prior Art

The penetrant inspection process utilizing fluorescent dyes in the penetrant has been highly developed over many decades. In essence, the surface of the workpiece to be tested is first flooded with a penetrant composition which normally consists of a hydrocarbon oil vehicle in which there is dissolved a fluorescent dye. After a sufficient dwell time during which the penetrant finds its way into surface flaws or flaws which open to the surface, excess penetrant is removed usually by means of a remover containing an agent which is an emulsifier for the oil of the penetrant. This step is followed by the application of a developer which may be a dry developer of very finely divided particles, or it may be a suspension of particles in an aqueous or non-aqueous medium. The developer particles serve to draw out the entrapped penetrant thereby rendering visible the location and extent of any flaws in which the penetrant had become lodged. Inspection of the piece is carried out under ultraviolet irradiation making the fluorescent dye deposits visible against a relatively dark background of the workpiece surface.

A penetrant inspection process is only as effective as the ability to determine the extent and location of trapped penetrant. Fluorescent containing penetrants have become very widely used because it is easier to locate a small deposit of fluorescent dye than it is to locate a deposit of visible dye with ordinary light. Fluorescent dyes, however, are quite expensive and amount to about 25 to 50% of the total penetrant cost. It, therefore, becomes economically inadvisable to increase the concentration of dye in the penetrant which would, of course, also increase the problems of disposal of excess fluorescent dye in the penetrant.

SUMMARY OF THE INVENTION

The present invention provides an improved method of enhancing fluorescent indications in a penetrant inspection process without utilizing a highly concentrated fluorescent dye in the penetrant composition. Instead, the present invention proceeds by using a penetrant having a hydrocarbon oil vehicle in which there is dissolved a normal amount of fluorescent dye. After the penetrant has become lodged in surface flaws, the excess is washed from the surface by any suitable means including a simple washing with water. Then a remover is applied for the purpose not only of emulsifying the penetrant vehicle remaining but also for reinforcing the concentration of fluorescent dye in the entrapped penetrant. This is accomplished by using a remover composition containing a fluorescent dye which is more soluble in the penetrant vehicle than it is in the remover vehicle. Consequently, when the remover contacts the entrapped penetrant, there is a preferential solubility exhibited by the penetrant for the dye in the remover and the relative concentration or the intensity of the fluorescent indication in the entrapped penetrant is enhanced.

DESCRIPTION OF THE PREFERRED EMBODIMENTS

In accordance with the present invention, any penetrant of the post-emulsifiable type can be used. A typical formula of such a penetrant is given below:

| | |
|---|---|
| Aromatic hydrocarbon solvent | 15% by weight |
| Phosphate type plasticizer | 30% by weight |
| Kerosene | 18% by weight |
| Fluorescent dye | 0.7% by weight |
| Paraffin oil | 36.3% by weight |

The remover composition of the present invention which forms one of the most important features thereof represents a controlled balance between emulsifiability and solvency. Most removers are supplied as concentrates, as explained in my previous U.S. Pat. No. 3,558,882 which is incorporated herein by reference. The remover compositions of that previous patent are fully useful in accordance with the present invention by adding a fluorescent dye or a fluorescent enhancing agent thereto. In the previous patent, there was described a concentrate consisting of a liquid, water-soluble nonionic surfactant, or mixture of surfactants, a water-immiscible aromatic hydrocarbon solvent having a Kauri-Butanol (KB) value of at least 70, and a normally liquid, water-miscible glycol-ether type of coupler. As a concentrate containing 75 to 100% of nonaqueous components, the composition functions as a fast-acting emulsifier. The concentrated form of the composition is capable of infinite dilution with water and has a high degree of tolerance toward the oily penetrant that remains on the workpiece. Consequently, the composition can be used with various techniques for cleaning the surfaces of the workpiece. When used as a spray, the concentrate can be diluted to a value between about 0.5 and 15% for effective use. When the concentrate is used in an undiluted state, it exhibits substantial emulsifying action toward the oily penetrant when in substantially static contact with the penetrant.

In accordance with the present invention, a fluorescent enhancing agent is added to the concentrate. This agent may be the same dye as is present in the penetrant or it may be a dye which is compatible therewith. For example, the dye in the penetrant does not have to be identical with that in the remover as long as the two dyes have similar spectral characteristics.

There are many dye materials which can be effectively used in the remover compositions of the present invention. The preferred material for use in both the penetrant and in the remover is methyl diaminocoumarin because it exhibits a substantial solubility in the remover vehicle, and does not crystallize out when the concentrate is diluted substantially with water. Other materials which are useful for the purpose of the present invention are fluorescent dyes such as fluoranthene, "Uvitex OB" (benzoxazole theophene), a fluorescent whitener which is very useful because of its hydrophobic characteristics, and fluorescent dyes such as "Hudson Yellow". In the case of some of these materials, their solubility is limited and it is advisable to keep the remover solution thoroughly agitated upon dilution so that the fluorescent agents do not settle out.

The composition of the remover is subject to wide variation. As mentioned, the remover preferably contains a nonionic surfactant which includes materials such as alkylphenoxy polyethoxylated ethanols in which the alkyl radical is usually from 8 to 12 carbon atoms in length and is preferably an octyl or nonyl radical, and in which the number of ethylene groups ranges from about 6 to 30 per molecule. If two or more such surfactants are used, one of them preferably contains about 9.5 ethylene oxide groups and the other or others contain about 12 to 30 ethylene oxide groups.

Another type of nonionic surfactant which has been found suitable for use in the remover is a liquid, water-miscible polyethoxylated straight chain primary alcohol containing from 12 to 15 carbon atoms per molecule and having 6.5 to 15.5 ethylene oxide groups per molecule of alcohol.

Still other surfactants which can be used are the low foaming, biodegradable nonionic surfactants which are primary alcohol-ethylene oxide adducts which have been modified to reduce foaming.

The water-immiscible aromatic hydrocarbon solvent should have a KB value of about 70 but solvents having higher KB values up to 120 or more are suitable provided the aromatic hydrocarbon solvents are properly balanced with respect to the other components to give a clear, homogeneous liquid.

As far as the glycol-ether couplers are concerned, I prefer to use one of the families of "Cellosolves" marketed by Union Carbide Corporation. Other glycol-ethers identified in the aforementioned U.S. Pat. No. 3,558,882 can also be employed. As far as the concentrated, nonaqueous remover composition is concerned, I prefer to use from 5 to 85% by weight surfactant, 5 to 20% by weight of the aromatic hydrocarbon solvent, and 15 to 90% by weight of the glycol type coupler. Preferred concentrates contain from 20 to 50% by weight surfactant, 12 to 18% by weight aromatic hydrocarbon solvent, and 30 to 50% by weight of the glycol type coupler.

The amount of fluorescent agent added to the concentrate will vary depending upon the relative solubility of the agent in the vehicle. In the case of methyl diaminocoumarin, this material is usually added in amounts ranging from a small fraction of 1% to as much as 8 or 9% by weight.

The oily penetrant is applied in the usual method to the surface of the workpiece and allowed to penetrate into any surface flaws. Then a prerinsing step is used in which much of the excess penetrant is removed. It is not critical at this stage that all of the excess penetrant be removed since the prewashing step is followed by a thorough emulsifying step. Consequently, the prewashing step can consist simply of rinsing with water with or without surfactants being present so that most of the mobile penetrant which has not found its way into flaws is removed.

Following the prewash, the test surface is ready for the application of the emulsifying remover. As noted previously, the remover can be used in the form of a relatively dilute concentration or it can be used as a concentrate. In most cases, I prefer to use a concentration of about 20 to 25%, in other words, 1 part of concentrate to either 3 or 4 parts of water.

The following specific examples are illustrative of the types of remover compositions which can be used in accordance with the present invention:

EXAMPLE I

| | |
|---|---|
| Nonylphenol poly (15) ethoxy ethanol | 16% |
| Nonylphenol poly (9.5) ethoxy ethanol | 23% |
| Aromatic hydrocarbon, such as xylene | 13% |
| Diethylene glycol monobutyl ether | 40% |
| Methyl diaminocoumarin | 8% |

EXAMPLE II

| | |
|---|---|
| Nonylphenoxy poly (12) ethoxylated alcohol | 42.8% |
| Diethylene gycol monobutyl ether | 42% |
| Aromatic hydrocarbon solvent, 70KB | 15% |
| "Uvitex OB" | 0.2% |

EXAMPLE III

| | |
|---|---|
| $C_{12}$—$C_{15}$ alcohol (15 ethylene oxide) | 20% |
| Lauroyl amide (5 ethylene oxide) | 22% |
| Aromatic hydrocarbon solvent, 70KB | 15% |
| Diethylene glycol monobutyl ether | 40% |
| Fluoranthene | 3% |

The compositions of the present invention conserve the use of fluorescent dyes which amount to about 25 to 50% of the total penetrant cost. The improved economy is achieved without sacrifice in results because the indications produced are at least as bright and usually brighter than indications produced using conventional fluorescent penetrant dye inspection processes.

It should be evident that various modifications can be made to the described embodiments without departing from the scope of the present invention.

I claim as my invention:

1. A method for the non-destructive testing for flaws on the surface of a workpiece which comprises:
   applying a penetrant composition including a fluorescent dye in a liquid vehicle onto said surface to permit said penetrant to become trapped in said flaws,
   removing excess penetrant from said surface while leaving penetrant entrapped in said flaws,
   applying a remover composition to said surface, said remover composition including a solvent, at least one surface active agent dissolved in said solvent, and a fluorescent material which is more readily soluble in said liquid vehicle than in said solvent, whereby said fluorescent material is preferentially absorbed in the penetrant entrapped in said flaws to thereby enhance the fluorescence of the entrapped penetrant, and
   applying a developer to the surface to draw the entrapped penetrant to the surface of the workpiece.

2. A method according to claim 1 in which said liquid vehicle in said penetrant is a hydrocarbon oil.

3. A method according to claim 1 in which said fluorescent dye in said penetrant composition is methyl diaminocoumarin.

4. A method according to claim 1 in which said solvent includes aromatic hydrocarbon.

5. A method according to claim 1 in which both said fluorescent dye in said penetrant composition and said fluorescent material in said remover include methyl diaminocoumarin.

6. A method according to claim 1 in which said excess penetrant is removed by water washing.

7. A method according to claim 1 in which:
   said surface active agent in said remover is an emulsifier for the liquid vehicle in said penetrant.

* * * * *